(12) United States Patent
Duignan et al.

(10) Patent No.: US 9,764,102 B2
(45) Date of Patent: Sep. 19, 2017

(54) DISPENSER CAP ARRANGEMENT

(71) Applicant: EURO-CELTIQUE S.A., Luxembourg (LU)

(72) Inventors: Cathal Duignan, Carrick on Shannon (IE); Peter Prior, Boyle (IE)

(73) Assignee: EURO-CELTIQUE S.A., Luxembourg (LU)

( * ) Notice: Subject to any disclaimer, the term of this patent is extended or adjusted under 35 U.S.C. 154(b) by 267 days.

(21) Appl. No.: 14/355,802

(22) PCT Filed: Oct. 31, 2012

(86) PCT No.: PCT/GB2012/052708
§ 371 (c)(1),
(2) Date: May 1, 2014

(87) PCT Pub. No.: WO2013/064820
PCT Pub. Date: May 10, 2013

(65) Prior Publication Data
US 2014/0311484 A1   Oct. 23, 2014

(30) Foreign Application Priority Data
Nov. 1, 2011 (GB) .................... 1118842.2

(51) Int. Cl.
*A61M 15/00* (2006.01)
*B65D 41/04* (2006.01)

(52) U.S. Cl.
CPC ...... *A61M 15/0026* (2014.02); *A61M 15/007* (2014.02); *A61M 15/009* (2013.01); *B65D 41/0414* (2013.01); *B65D 41/0428* (2013.01)

(58) Field of Classification Search
None
See application file for complete search history.

(56) References Cited

U.S. PATENT DOCUMENTS

| | | | |
|---|---|---|---|
| 3,380,610 A * | 4/1968 | Krieps | B65D 43/0218 215/320 |
| 3,405,837 A | 10/1968 | Carpenter | |
| 3,742,898 A * | 7/1973 | Souza | B65D 39/04 116/268 |
| 3,753,510 A | 8/1973 | Hedgewick et al. | |
| 3,876,102 A * | 4/1975 | Wharton | B65D 39/12 215/270 |
| 4,341,320 A | 7/1982 | Libit | |
| 4,504,009 A | 3/1985 | Boik et al. | |

(Continued)

FOREIGN PATENT DOCUMENTS

| | | |
|---|---|---|
| CN | 1133584 A | 10/1996 |
| CN | 101065295 A | 10/2007 |

(Continued)

OTHER PUBLICATIONS

International Search Report for PCT/GB2012/052708 mailed Jun. 6, 2013.

(Continued)

*Primary Examiner* — Tan-Uyen (Jackie) T Ho
*Assistant Examiner* — Joseph D Boecker
(74) *Attorney, Agent, or Firm* — Nixon & Vanderhye P.C.

(57) ABSTRACT

Dispenser cap arrangements for enclosing a portion of a dispenser of a medicament are described herein.

29 Claims, 9 Drawing Sheets

(56) References Cited

U.S. PATENT DOCUMENTS

| | | | | |
|---|---|---|---|---|
| 4,966,302 | A | * | 10/1990 | Hjordie ............... B65D 43/0218 220/268 |
| 4,981,233 | A | * | 1/1991 | Scheurer ............... B65B 31/046 141/65 |
| 5,060,643 | A | | 10/1991 | Rich et al. |
| 5,421,482 | A | | 6/1995 | Garby et al. |
| 5,611,444 | A | | 3/1997 | Garby et al. |
| 5,819,968 | A | * | 10/1998 | Jones ..................... B65D 41/06 116/309 |
| 5,823,372 | A | * | 10/1998 | Levine ................... B65D 51/24 215/228 |
| 5,853,109 | A | * | 12/1998 | Elliott ................ B65D 47/0809 222/556 |
| 5,870,806 | A | | 2/1999 | Black, Jr. |
| 6,202,642 | B1 | | 3/2001 | McKinnon et al. |
| 6,422,234 | B1 | | 7/2002 | Bacon |
| 6,729,487 | B1 | * | 5/2004 | Dischler ............... B65D 41/065 215/204 |
| 6,866,038 | B2 | | 3/2005 | Bacon |
| 7,036,505 | B2 | | 5/2006 | Bacon et al. |
| 7,047,964 | B2 | | 5/2006 | Bacon |
| 7,195,134 | B2 | | 3/2007 | Ouyang |
| 7,225,805 | B2 | | 6/2007 | Bacon |
| 7,814,900 | B2 | | 10/2010 | Bacon |
| 7,909,236 | B2 | | 3/2011 | Erdie |
| 8,308,028 | B2 | | 11/2012 | Bacon |
| 8,329,271 | B2 | | 12/2012 | Bacon |
| 8,408,208 | B2 | | 4/2013 | Bacon |
| 2003/0029890 | A1 | * | 2/2003 | Olechowski ........... B65D 47/10 222/525 |
| 2004/0025868 | A1 | * | 2/2004 | Bruna ................ A61M 15/009 128/200.23 |
| 2004/0069301 | A1 | | 4/2004 | Bacon |
| 2005/0053832 | A1 | * | 3/2005 | Ray ..................... H01M 2/0413 429/181 |
| 2007/0251950 | A1 | * | 11/2007 | Bacon ................ A61M 15/009 221/8 |
| 2008/0017642 | A1 | | 1/2008 | King |
| 2008/0135576 | A1 | * | 6/2008 | Bacon ................ A61M 15/009 222/36 |
| 2008/0173609 | A1 | * | 7/2008 | Shingle ................ B65D 50/066 215/201 |
| 2008/0178872 | A1 | | 7/2008 | Genova et al. |
| 2010/0012115 | A1 | | 1/2010 | Bacon |
| 2012/0017900 | A1 | | 1/2012 | Bacon |
| 2012/0085793 | A1 | * | 4/2012 | Selina ................ B65D 47/063 222/529 |
| 2012/0090621 | A1 | * | 4/2012 | van der Houwen ........... A61M 16/0468 128/207.16 |
| 2012/0111323 | A1 | | 5/2012 | Bacon et al. |
| 2016/0038696 | A1 | * | 2/2016 | Duignan ........... A61M 15/0026 128/200.23 |

FOREIGN PATENT DOCUMENTS

| | | | |
|---|---|---|---|
| EP | 0414536 | 2/1991 | |
| FR | 1082285 | 12/1954 | |
| FR | 2375104 | 7/1978 | |
| GB | WO 0128881 A1 * | 4/2001 | ............ B65D 39/12 |
| JP | 63-258763 A | 10/1988 | |
| JP | 2004-507328 A | 3/2004 | |
| JP | 2005-510423 A | 4/2005 | |
| JP | 2007-524435 A | 8/2007 | |
| JP | 2008-520305 | 6/2008 | |
| JP | 2009-507541 A | 2/2009 | |
| TW | 201014623 | 4/2010 | |
| WO | WO 9414588 A1 * | 7/1994 | ............ B29C 33/48 |
| WO | WO 95/08484 | 3/1995 | |
| WO | WO 02/17999 | 3/2002 | |
| WO | WO03/045806 A1 | 6/2003 | |
| WO | 03/080161 | 10/2003 | |
| WO | WO2004/078236 A2 | 9/2004 | |
| WO | 2005/028006 | 3/2005 | |
| WO | WO 2006/054083 | 5/2006 | |
| WO | 2007/022573 | 3/2007 | |
| WO | 2007/029019 | 3/2007 | |
| WO | WO2007/029019 A1 | 3/2007 | |
| WO | WO 2010/005946 | 1/2010 | |

OTHER PUBLICATIONS

Written Opinion of the International Searching Authority mailed Jun. 6, 2013.
International Preliminary Report on Patentability dated May 6, 2014 with Written Opinion, issued in corresponding International Application No. PCT/GB2012/052708.
English Machine translation of JPS63-258763A (Oct. 1998) obtained from EPO website.

* cited by examiner

DISPENSER CAP ARRANGEMENT

This application is the U.S. national phase of International Application No. PCT/GB2012/052708 filed 31 Oct. 2012 which designated the U.S. and claims priority to GB 1118842.2 filed 1 Nov. 2011, the entire contents of each of which are hereby incorporated by reference.

FIELD OF THE INVENTION

The present invention relates to a dispenser cap arrangement for enclosing a portion of a dispenser of a medicament. In particular, the present invention relates to a dispenser cap arrangement, a dispenser cap, a dispenser cap closure device, a method of closing a dispenser, and a closure arrangement.

BACKGROUND OF THE INVENTION

In general, metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user.

We have previously described a number of dispensers, see for example U.S. Pat. No. 7,721,731. However, it has been found that manufacturing tolerances mean that the length of a container or substance source can vary from container to container. Furthermore, the length of the spout of the container may vary, too.

This can cause problems in dispenser devices wherein the aerosol can is stationary and another part is moved relative to the can to displace its valve and dispense medicament. Typically the other moving part can only move a certain distance (i.e. a predetermined amount of travel) which means that if, for example a can or its valve is relatively short, the valve may not be fully displaced. As a result, a full dose of medicament may not be dispensed.

There have been different approaches taken to overcoming this problem. See, for example, WO2003/080161 or WO2007/029019.

In the above-mentioned previous approaches, the dispenser body and cap are a constant size and the canister is placed in the body at the same position in all dispensers. The variation in the resulting space between the end of the canister and the cap is taken by deformable materials placed atop the container. However, the above solutions do not always provide satisfactory results, so we have appreciated the need for an improved dispenser cap arrangement.

STATEMENT OF THE INVENTION

The present invention therefore provides a dispenser cap arrangement for enclosing a portion of a dispenser of a medicament, the dispenser cap arrangement comprising: a dispenser cap comprising a hollow body having a lower open end for engaging with a body portion of a dispenser, and an upper open end for receiving a cap closure device for closing the upper open end, the upper open end comprising an engageable portion; and a cap closure device, comprising: an upper cap closure portion for engaging with the upper open end of the dispenser cap to close the upper open end of the dispenser cap; a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap.

The cap, in combination with the closure device, provide a means of enclosing a portion of a dispenser. Advantageously, the bistable portion of the closure device that is switchable between two stable forms (extended and collapsed) enables the closure device to be inserted and the cap closed when the closure device is in the desired position relative to the cap. Furthermore, the cap closure device, once in a stable form, requires a force to be applied to the upper closure portion to switch between the stable forms. As such, once in the collapsed form, the closure device is difficult to remove from the cap, thereby securing the closure device to the cap so that it cannot easily be removed. Furthermore, by using the above-mentioned cap closure device, a dispenser is able to be assembled where the medicament container of a dispenser can be fixed in the body in such a position that reliable and reproducible dosing can be achieved regardless of differences in the length of the spout and/or length of the container due to manufacturing tolerances.

In embodiments of the dispenser cap arrangement, the bistable portion of the cap closure device comprises: a substantially rigid separator connected to the upper cap closure portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of a force to the upper cap closure portion and lower cap closure portion so as to permit a change of form of the dispenser cap closure device between the first stable form and second stable form. Such a configuration advantageously provides the cap closure device with the ability to be switched between the two stable forms.

Preferably, an angle defined between an outer surface of the substantially rigid separator and the resiliently deformable separator is acute when in the second stable form, and obtuse when in the first stable form.

In further embodiments of the dispenser cap arrangement, the lower cap closure portion comprises a plurality of protrusions extending radially outwards having an upper surface for engaging with the engageable portion of the dispenser cap, and wherein a lower surface of the lower cap closure portion is engageable with a surface of a medicament container in a dispenser. The plurality of protrusions extending from the lower cap closure portion thus provide a means to secure the cap closure portion to the cap.

Preferably, the engageable portion of the dispenser cap comprises a ramped portion, and wherein the ramped portion and the protrusions on the lower cap closure portion are configured such that rotation of the cap closure device causes the upper surface of the plurality of protrusions to ride along the ramped portion so as to draw the cap closure device further into the dispenser cap. Preferably, when the cap closure device is rotated, the riding of the upper surface of the protrusions along the ramped portion causes the lower surface of the lower cap closure portion to drive down onto a medicament container in a dispenser.

By providing the ramped portions, the protrusions on the lower cap closure portion of the cap closure device may ride along the ramped portion and thus be drawn into the cap during rotation of the cap closure device. The position of the cap closure device relative to the cap may thus be adjusted prior to the bistable portion being switched from the extended to the collapsed forms. As such, tolerances in the length of the container or the container spout in the dispenser may be accounted for prior to final assembly of the dispenser.

In embodiments with the ramped portion, the ramped portion comprises a plurality of ramped portions around the circumference of a lip of the dispenser cap, the plurality of ramped portions equalling the number of plurality of protrusions on the lower cap portion of the cap closure device. Preferably, the ramped portions are separated from one and other by a gap having a width that is greater than or equal to the width of a protrusion on the lower cap closure portion.

In further embodiments, of the dispenser cap arrangement, an upper surface of the dispenser cap comprises a limiting means for preventing rotation of the cap closure device when in the second stable form. Preferably, the limiting means comprises a plurality of teeth located on an upper surface of the dispenser cap, and wherein the dispenser cap closure device comprises a plurality of protrusions on a lower surface of the upper cap closure portion, the teeth and protrusions being configured to engage with one another so as to prevent rotation of the cap closure device when in the second stable form.

By providing a limiting means, further rotation of the cap closure device, once in the collapsed state, may be prevented. As such, the cap closure device is prevented from rotating further into, or out of the cap. The cap closure device is thus secured in place.

In some embodiments, the dispenser cap may comprise one or more protrusions in the upper open end of the dispenser cap, the one or more protrusions being arranged to engage with a correspondingly shaped recess in the upper cap closure portion when the dispenser cap is closed by the dispenser closure device. Such an arrangement helps retain the dispenser cap closure device in place once inserted into the end of the dispenser cap.

The present invention also provides a dispenser cap closure device for closing an end of a dispenser cap of a medicament dispenser, the cap closure device comprising: an upper cap closure portion for engaging with an upper open end of a dispenser cap to close an open end of a dispenser cap; a lower cap closure portion for engaging with a an engageable portion of the upper open end of a dispenser cap to secure the cap closure device to a dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when in the second stable form, the upper cap closure portion and lower cap closure portion are brought closer together.

The dispenser cap closure device advantageously comprises the bistable portion, which enables the cap closure device to be switched between two stable forms. Furthermore, by using the above-mentioned cap closure device, a dispenser is able to be assembled where the medicament container of a dispenser can be fixed in the body in such a position that reliable and reproducible dosing can be achieved regardless of differences in the length of the spout and/or length of the container due to manufacturing tolerances.

In embodiments of the dispenser cap closure device, the bistable portion comprises: a substantially rigid separator connected to the upper cap portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of an opposing force between the upper cap closure portion and lower cap closure portion so as to permit a change of form of the dispenser cap closure device between the first stable form and second stable form. Such a configuration advantageously provides the cap closure device with the ability to be switched between the two stable forms.

Preferably, an angle defined between an outer surface of the substantially rigid separator and the resiliently deformable separator is acute when in the second stable form, and obtuse when in the first stable form.

In further embodiments of the dispenser cap closure device, the lower cap closure portion comprises a plurality of protrusions extending radially outwards having an upper surface for engaging with an engageable portion of a dispenser cap, and wherein a lower surface of the lower cap closure portion is engageable with a surface of a medicament container in a dispenser. Preferably, the protrusions are substantially equally-spaced circumferentially around the lower cap closure portion.

In some embodiments of the dispenser cap closure device, the dispenser cap closure device comprises a plurality of protrusions on a lower surface of the upper cap closure portion for engaging with correspondingly-spaced teeth on a dispenser cap for preventing rotation of the dispenser cap closure device when in the collapsed state.

In further embodiments, the upper cap closure portion comprises a recess in the upper cap closure portion that is arranged to engage with a correspondingly shaped protrusion in an upper open end of a dispenser cap. Such an arrangement helps retain the dispenser cap closure device in place once inserted into the end of the dispenser cap.

The present invention also provides a dispenser cap for enclosing a portion of a dispenser of a medicament, the dispenser cap comprising: a hollow body having a lower open end for engaging with a body portion of a dispenser, and an upper open end for receiving a dispenser cap closure device for closing the upper open end, wherein the upper open end comprises an engageable portion for engaging with a dispenser cap closure device for closing the upper open end of the hollow body. For example, the dispenser cap could be the dispenser cap as described above.

By using the above-mentioned dispenser cap, a dispenser cap closure device may be used such that a dispenser is able to be assembled where the medicament container of a dispenser can be fixed in the body in such a position that reliable and reproducible dosing can be achieved regardless of differences in the length of the spout and/or length of the container due to manufacturing tolerances.

In embodiments of the dispenser cap, the engageable portion comprises a plurality of ramped portions around the circumference of the dispenser cap. Preferably, each of the ramped portions is separated by a gap.

In some embodiments, the dispenser cap has an upper surface of the dispenser cap that comprises a limiting means for preventing rotation of a dispenser cap closure device when engaged with the dispenser cap. In such embodiments, the limiting means comprises a plurality of teeth located on the upper open end of the dispenser cap, the teeth for engaging with one or more protrusions on a dispenser cap closure device so as to prevent rotation of a dispenser cap closure device when engaged.

In further embodiments, the dispenser cap may comprise one or more protrusions in the upper open end of the dispenser cap, the one or more protrusions being arranged to engage with a correspondingly shaped recess in an upper cap closure portion of a dispenser cap closure device for closing the dispenser cap. Such an arrangement helps retain the dispenser cap closure device in place once inserted into the end of the dispenser cap.

The present invention also provides a dispenser for dispensing a dose of medicament from a substance source, the dispenser comprising: a body for receiving a substance source, the body having a mouthpiece through which a medicament is dispensable; a substance source comprising a container containing a medicament to be dispensed; a dispenser cap arrangement as described above, wherein the dispenser cap arrangement is coupled to the body for enclosing the substance source. Such a dispenser may thus be closed using the cap closure device comprising the bistable portion, such that it may not be opened by a user or tampered with once closed.

By using the above-mentioned cap closure device, the dispenser can be assembled where the medicament container can be fixed in the body in such a position that reliable and reproducible dosing can be achieved regardless of differences in the length of the spout and/or length of the container due to manufacturing tolerances.

In embodiments of the dispenser, the substance source is a pressurised metered-dose inhaler (pMDI).

In further embodiments of the dispenser, the dispenser further comprises a dose counter for indicating a number of actuations of the dispenser corresponding to a number of doses dispensed from the substance or, or a number of doses remaining in the substance source. Advantageously, the dose counter enables the user to determine how many doses remain in the dispenser so that the user knows when to obtain a replacement dispenser.

The present invention further provides a method of closing a dispenser for dispensing a dose of medicament from a substance source, the dispenser comprising: a body for receiving a substance source, the body having a mouthpiece through which a medicament is dispensable; a substance source comprising a container containing a medicament to be dispensed; and a dispenser cap arrangement for coupling to the body for enclosing the substance source, the dispenser cap arrangement comprising a dispenser cap and dispenser cap closure device, the method comprising the steps of: inserting the substance source into the body of the dispenser and affixing the dispenser cap to the body of the dispenser, or vice versa; inserting the dispenser cap closure device into an upper open end of the dispenser cap; applying a force to the dispenser cap closure device to switch a bistable portion of the dispenser cap closure device from a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap. The bistable portion of the cap closure device thus enables the dispenser to be closed.

By using the above-mentioned cap closure device, a dispenser is able to be assembled where the medicament container of a dispenser can be fixed in the body in such a position that reliable and reproducible dosing can be achieved regardless of differences in the length of the spout and/or length of the container due to manufacturing tolerances.

In embodiments of the method, the method further comprises rotating the dispenser cap closure device prior to the step of applying a force, such that a plurality of protrusions extending radially outwardly from a lower cap closure portion of the dispenser cap closure device engage with a ramped portion on a lower lip of the upper open end of the dispenser cap. Thus the cap closure portion is secured to the cap so that it cannot be removed.

The present invention also provides a closure arrangement for enclosing an article, the closure arrangement comprising: a hollow body for enclosing an article, having an upper open end for receiving a closure device for closing the upper open end, the upper open end comprising an engageable portion; and a closure device, comprising: an upper closure portion for engaging with the upper open end of the hollow body to close the upper open end of the hollow body; a lower closure portion for engaging with the engageable portion to secure the closure device to the hollow body; and a bistable portion connecting the upper closure portion and the lower closure portion, the bistable portion being switchable between a first stable form in which the bistable portion is extended, and a second stable form in which the bistable portion is collapsed, wherein, when the bistable portion is in the second stable form, the upper closure portion engages with the upper open end of the hollow body to close the upper open end of the hollow body such that an article in the hollow body is enclosed.

The hollow body, in combination with the closure device, provide a means of enclosing an article. Advantageously, the bistable portion of the closure device that is switchable between two stable forms (extended and collapsed) enables the closure device to be inserted and hollow body closed when the closure device is in the desired position relative to the hollow body. Furthermore, the closure device, once in a stable form, requires a force to be applied between the upper and lower closure portions to switch between the stable forms. As such, once in the collapsed form, the closure device is difficult to remove from the hollow body, thereby securing the closure device to the hollow body so that it cannot easily be removed. Furthermore, by using the above-mentioned closure device, an article may be assembled where the a device of an article can be fixed in the body in such a position that reliable and reproducible operation may be achieved regardless of differences in the length of the article due to manufacturing tolerances.

In embodiments of the closure arrangement, the bistable portion of the closure device comprises: a substantially rigid separator connected to the upper closure portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of a force to the upper closure portion so as to permit a change of form of the closure device between the first stable form and second stable form. This configuration enables the bistable portion to be switchable between the two stable forms.

Preferably, an angle defined between an outer surface of the substantially rigid separator and the resiliently deformable separator is acute when in the second stable form, and obtuse when in the first stable form.

In some embodiments of the closure arrangement, the lower closure portion comprises a plurality of protrusions extending radially outwards having an upper surface for engaging with the engageable portion of the hollow body, and wherein a lower surface of the lower lid closure portion is engageable with a surface of an article to be enclosed. The plurality of protrusions extending from the lower closure portion thus provide a means to secure the closure portion to the hollow body.

Preferably, the engageable portion comprises a ramped portion, and wherein the ramped portion and protrusions on the lower closure portion are configured such that rotation of the closure device causes the upper surface of the plurality of protrusions to ride along the ramped portion so as to draw the closure device further into the hollow body. Preferably, when the closure device is rotated, the riding of the upper surface of the protrusions along the ramped portion causes the lower surface of the lower closure portion to drive down onto an article to be enclosed.

By providing the ramped portions, the protrusions on the lower closure portion of the closure device may ride along the ramped portion and thus be drawn into the hollow body during rotation of the closure device. The position of the closure device relative to the hollow body may thus be adjusted prior to the bistable portion being switched from the extended to the collapsed form.

In embodiments of the closure arrangement, the ramped portion comprises a plurality of ramped portions around the circumference of a lip of the hollow body, the plurality of ramped portions equalling the number of plurality of protrusions on the lower lid portion of the lid closure device. Preferably, the ramped portions are separated from one another by a gap having a width that is greater than or equal to the width of a protrusion on the lower closure portion.

In further embodiments of the closure arrangement, an upper surface of the hollow body comprises a limiting means for preventing rotation of the closure device when in the second stable form.

By providing a limiting means, further rotation of the closure device, once in the collapsed state, may be prevented. As such, the closure device is prevented from rotating further into, or out of the hollow body. The closure device is thus secured in place.

Preferably, the limiting means comprises a plurality of teeth located on an upper surface of the hollow body, and wherein the closure device comprises a plurality of protrusions on a lower surface of the upper closure portion, the teeth and protrusions being configured to engage with one another so as to prevent rotation of the closure device when in the second stable form.

In some embodiments, the hollow body may comprise one or more protrusions in the upper open end of the hollow body, the one or more protrusions being arranged to engage with a correspondingly shaped recess in the upper closure portion when the hollow body is closed by the closure device. Such an arrangement helps retain the closure device in place once inserted into the end of the hollow body.

The present invention also provides a closure device for sealing an opening in a body comprising: a first portion for sealing an opening; a second portion, and a connecting portion connecting the first and second portions, the second portion being adapted to secure the device to a body, the connecting portion being adapted to switch from a first configuration to a second configuration upon application of a force to the device, wherein in the first configuration the device can be applied to and secured to a body and in the second configuration the first portion will seal an opening in the body.

By using the above-mentioned closure device, a dispenser is able to be assembled where the medicament container of a dispenser can be fixed in the body in such a position that reliable and reproducible dosing can be achieved regardless of differences in the length of the spout and/or length of the container due to manufacturing tolerances.

Preferably, in the second configuration the first portion and the second portion are closer to each other than in the first configuration.

The present invention further provides an enclosure arrangement for enclosing an article comprising: a hollow body for receiving an article and having an upper open end, a closure device, as described above, for sealing said open end, wherein the hollow body and the closure device have respective engageable portions for securing the body and device together, and in the second configuration the second portion of the closure device is adapted to contact an article in the body and the first portion of the closure device is adapted to seal the opening in the upper end of the body.

Preferably, the engageable portions are adapted to secure the hollow body and closure device together upon relative rotation of the body and device.

LIST OF FIGURES

The present invention will now be described, by way of example only, and with reference to the drawings, in which:

FIG. 7 is a cut-through view of the dispenser cap of FIG. 5 through axis X-X of FIG. 6a;

Figures 11A, 11B:
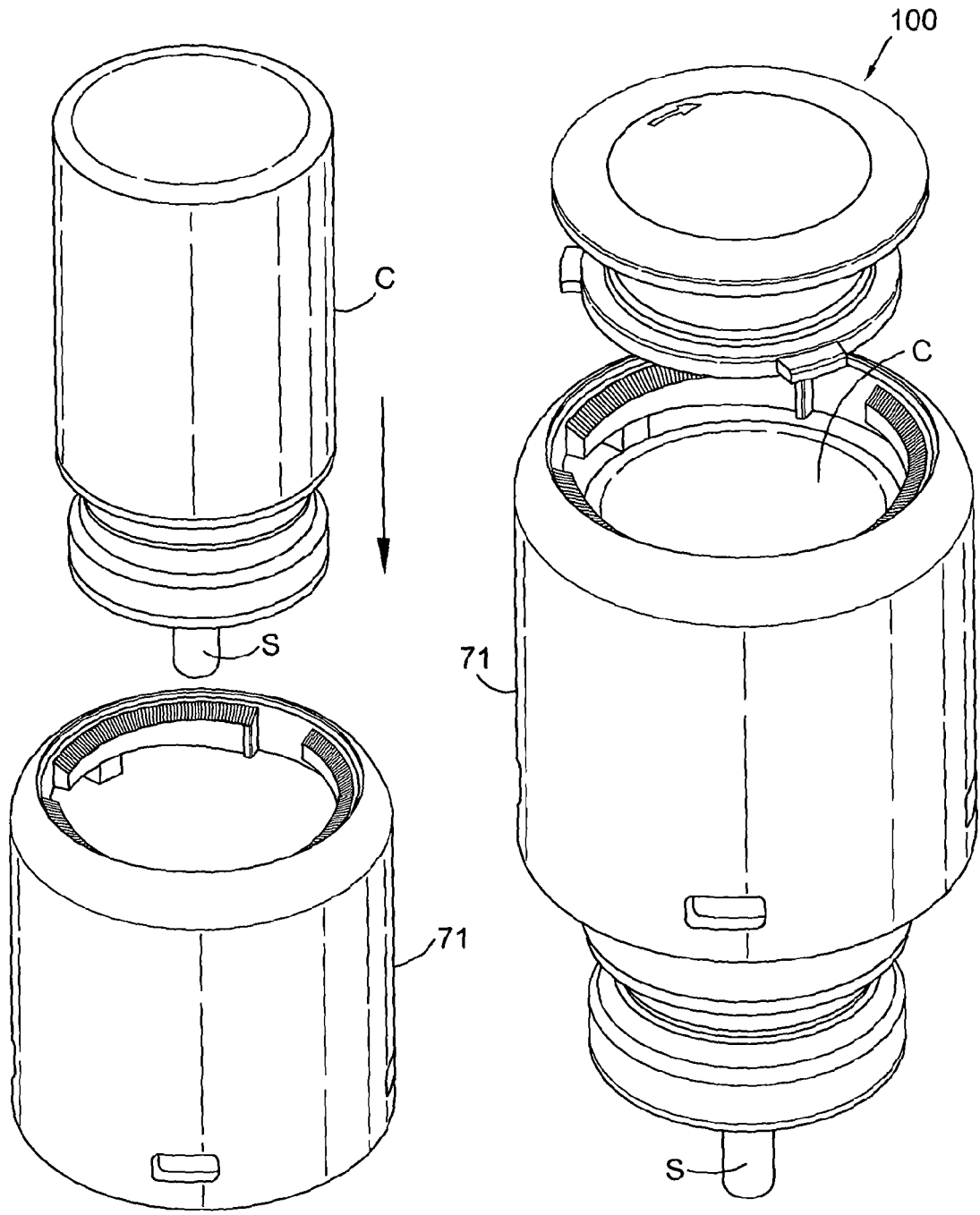
Figure 11C:
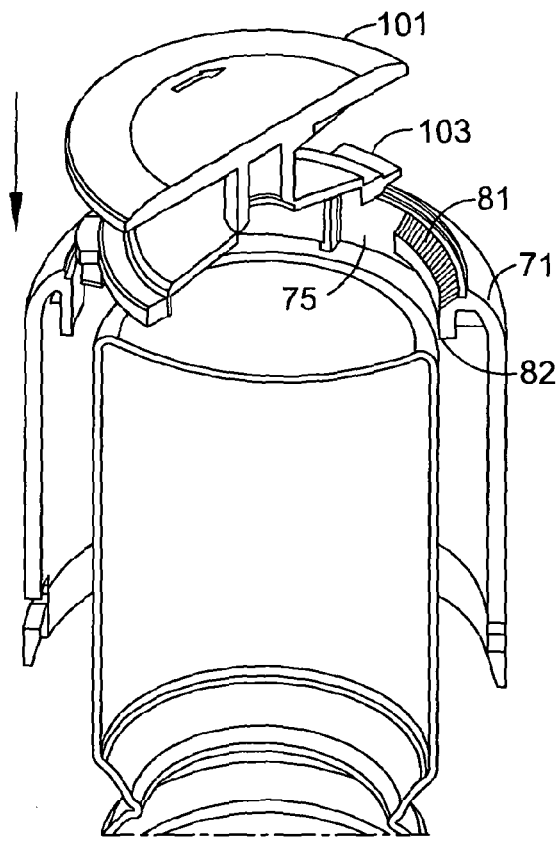
Figure 11D:
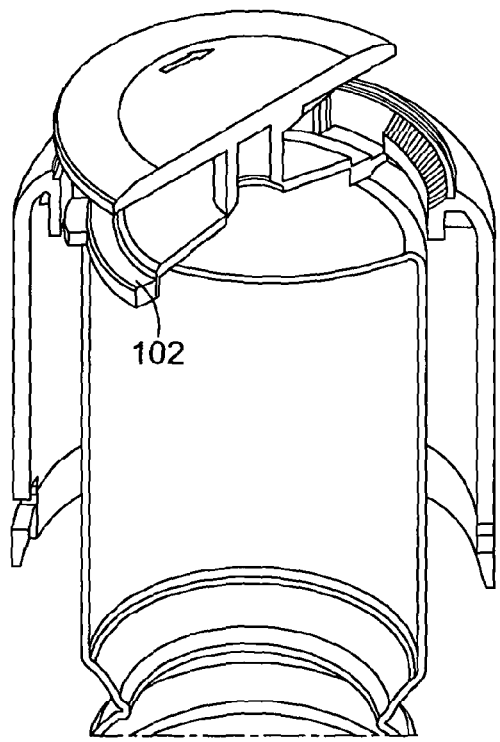
Figure 11E:
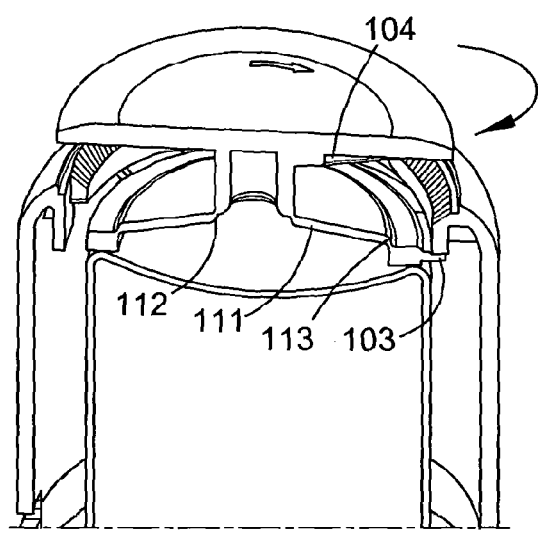
Figure 11F:
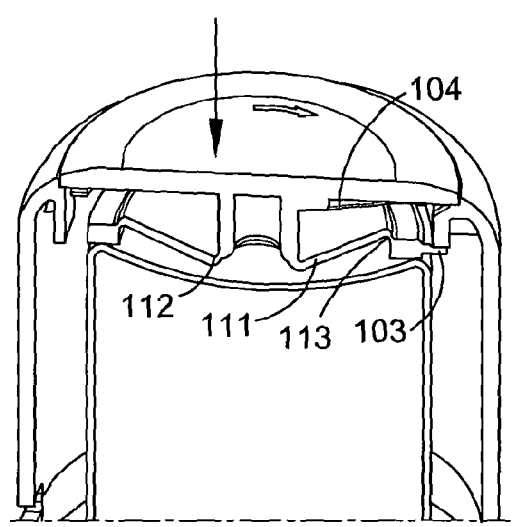
Figure 12:
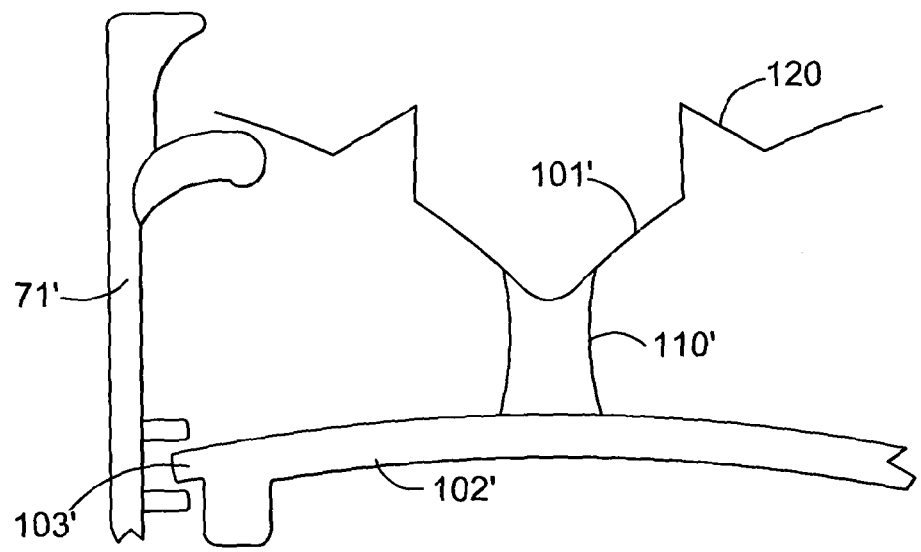

FIGS. 11 a to 11f show a sequence of steps of the dispenser cap assembly; and FIG. 12 shows an alternative closure device.

DETAILED DESCRIPTION OF THE PREFERRED EMBODIMENTS

Figure 1:
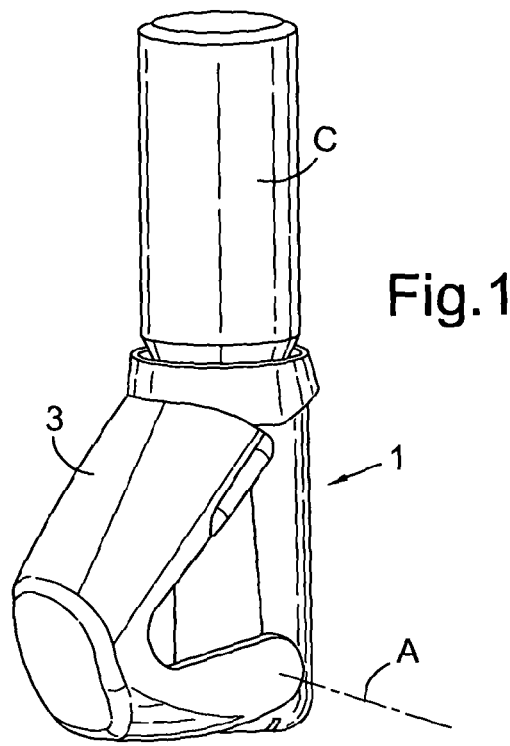
FIG. 1 is a perspective view of a dispenser in a closed configuration.
Figure 2:
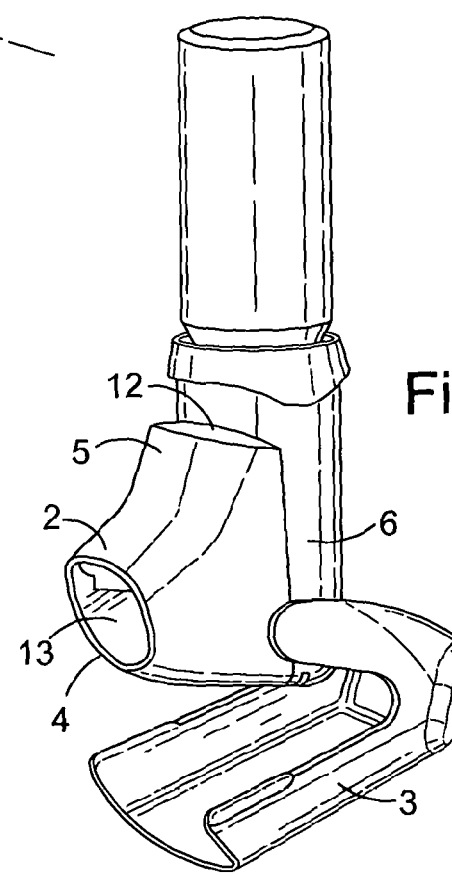
FIG. 2 is a similar view of the dispenser in open configuration.
Figure 3:
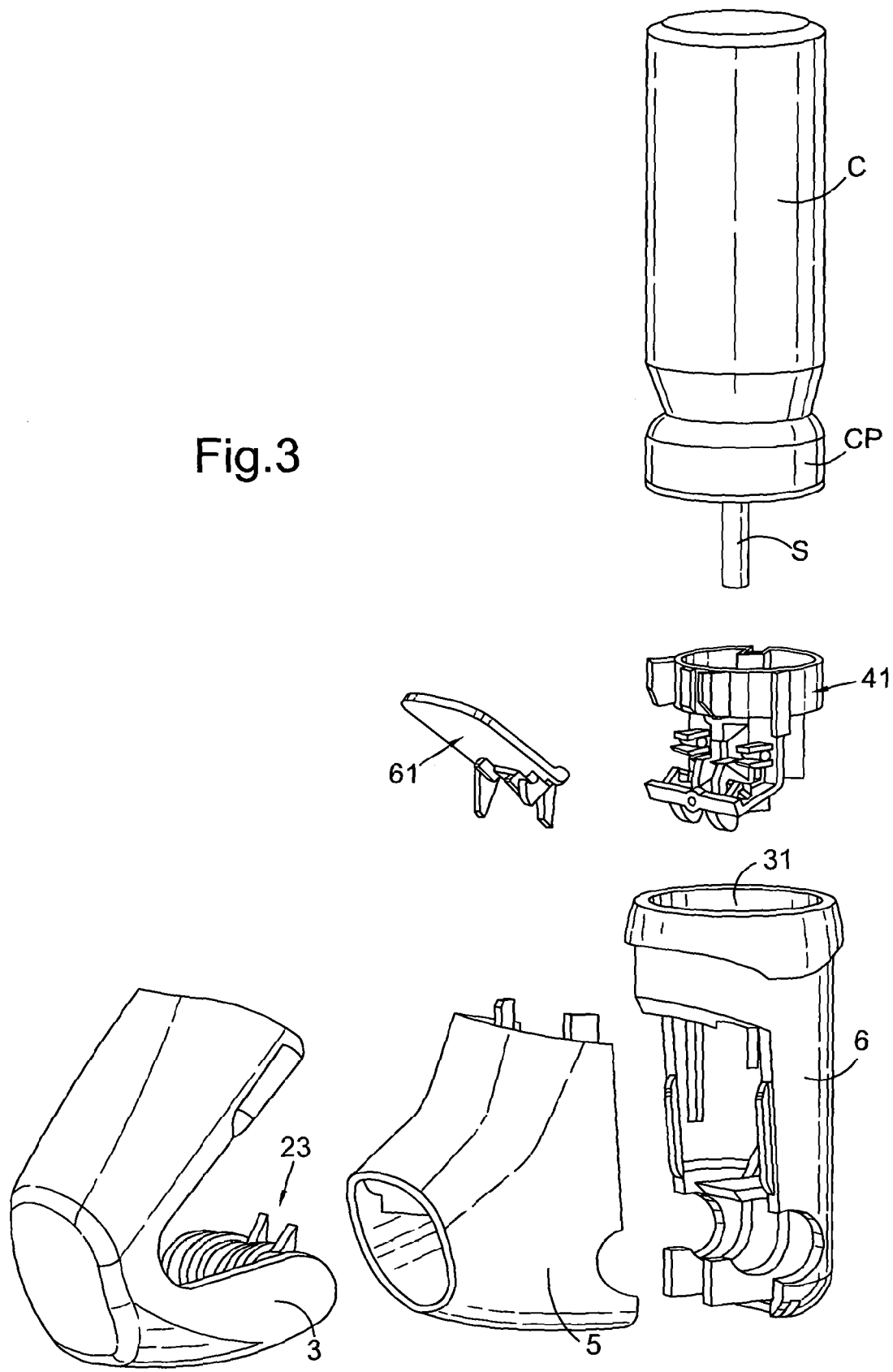
FIG. 3 is an exploded view of a prior version of the dispenser.
Figure 4:
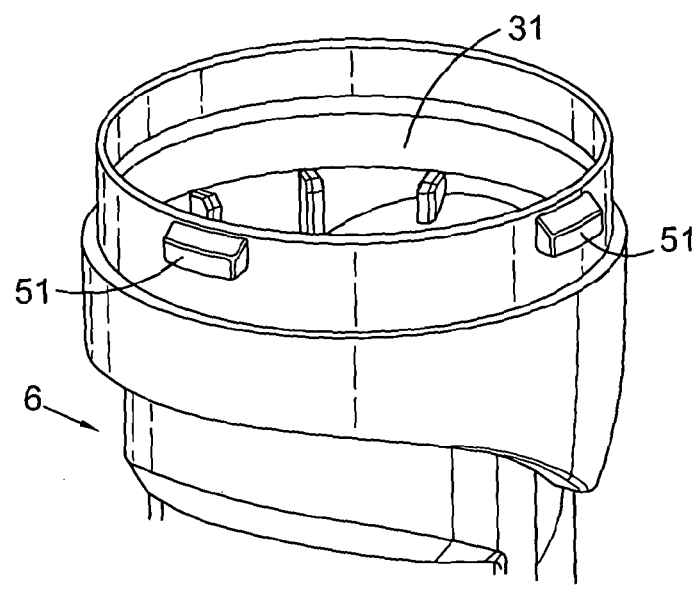
FIG. 4 shows an upper portion of a preferred main body part of the dispenser.

Referring first to FIGS. 1 to 4 of the drawings (of which FIGS. 1 to 3 are taken from our corresponding granted patent U.S. Pat. No. 7,721,731), the dispenser has a body 1 with a mouthpiece 2 and a pivoted mouthpiece cover 3. The mouthpiece is formed as an aperture 4 in a separate body part 5 clipped to a main body part 6 (although the skilled reader would appreciate that this formation could be made using a single-moulded piece). The main part 6 has upper and lower formations and the mouthpiece part has upper and lower complementary formations which engage when the mouthpiece part is slid from below to engage with the main part. The separate body part 5 has a cutaway with respect to the main body part 6, to define an air inlet 12 exposed by the cover 3 when this is opened. A medicament can C sits inside the body part 6. Immediately within the air inlet 12 is a guard 13 against fingers.

The cover 3 is pivoted about an axis A low in the body 6 at the joint between the two body parts. Integrally moulded with the cover 3 is a C section shaft. The shaft carries a cam arrangement 23, comprising two cam lobes, together with two fingers, a central one and an outer one. The latter is integral with one of a pair of discs, between which are the cam lobes, the shaft is bearingly supported by part circular journals in flanges integrally moulded within the main body part 6.

The body parts 5,6, and the cover 3 (with the shaft and cam arrangement) in the described embodiments are of moulded polypropylene material, whereby they can be fitted together with a modicum of flexure.

The can C is held in an opening 31 at the upper end of the main body part 6, where the body part extends completely around a valve crimp portion CP of the can C. A dispenser cap (not shown) couples to the main body part 6 to surround and encase the upper exposed end of the can C. The dispenser cap is coupled to the main body part 6 for example by means of protrusions 51. Other fixing means may be used so long as the main body part and dispenser cap are engaged together so that they do not come apart easily.

A junction member 41 is slidably accommodated in the body. The junction member also is of moulded polypropylene. Centrally, the junction member has a socket for an outlet stem S of the can C. The socket is continued by a passage, which has a thin wall, kinkable portion and a nozzle end (moveable outlet member), which is coupled to a nozzle. When the kinkable portion is unkinked, a medicament dispensed from the can stem into the passage is released through the nozzle and into a mouthpiece of the dispenser.

In operation, rotation of the mouthpiece cover 3 about the axis A causes the cam 23 to impart an upward force on the junction member 41. The resulting upward movement of the junction member 41 actuates the outlet stem S of the can, which dispenses a dose of medicament into the junction member and into the kink valve. The dispenser is now primed and ready with a dose of medicament.

Upon inhalation by a user through the mouthpiece 5, air drawn through the air inlet 12 impresses on the flap 61 causing the flap to move and release the junction member 41, which allows the kink valve to un-kink (due to the resilience of the passageway making up the kink valve, and the pressure of the medicament in the valve) to release the dose of medicament into the mouthpiece. Continued inhalation by the user causes the dose of medicament to be drawn out of the mouthpiece and delivered to the user.

After inhalation, the user closes the mouthpiece cover, and the junction member 41 and flap 61 return to their initial, un-primed, positions.

As discussed above, tolerances in the length of the can and its spout and in other components with which the can is in contact mean that the can is not always seated in the same position relative to the body and a dispenser cap (not shown in FIGS. 1 to 4, but the cap surrounds the upper portion of the can and is coupled to the main body part 6). Since the can C is preferably seated so that the movement of the junction member is able to effect dispensing of a precise dose of medicament, there is need of a device to take up the variable height of the can C and/or its spout relative to the body.

We will now describe a dispenser cap arrangement, dispenser cap closure device and dispenser cap that has been designed to take up these tolerances and to allow the dispenser to work as intended.

Figure 5:
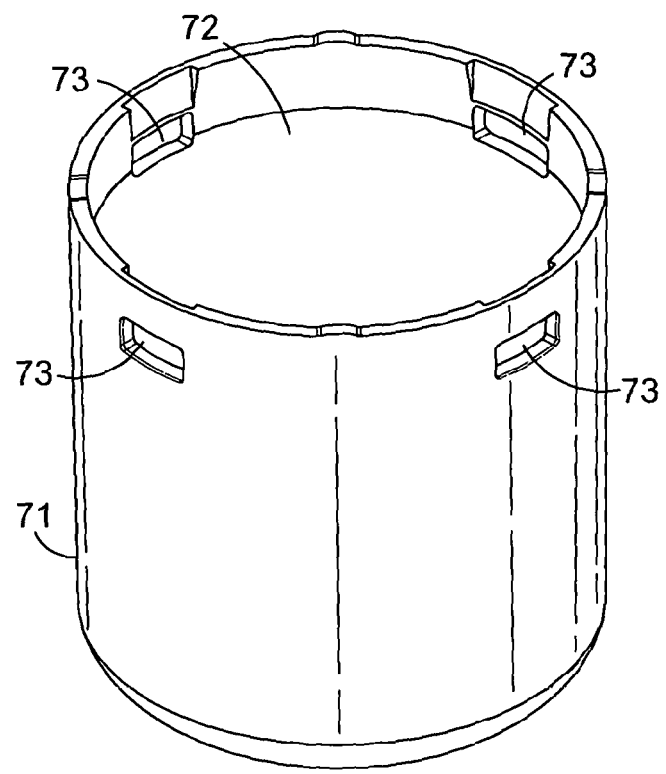
FIG. 5 is an underside view of a preferred dispenser cap.
Figure 6A:
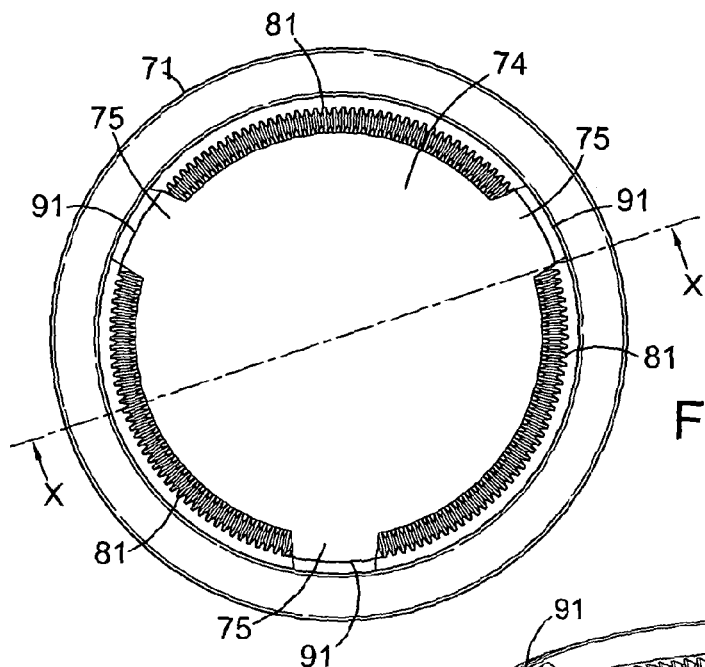
FIG. 6a is an upper-end view of the dispenser cap of FIG. 5.
Figure 6B:
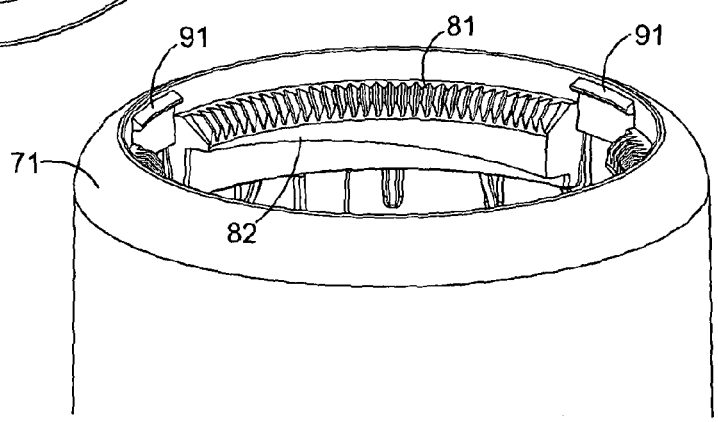
FIG. 6b is a perspective view of the dispenser cap of FIG. 5.
Figure 7:
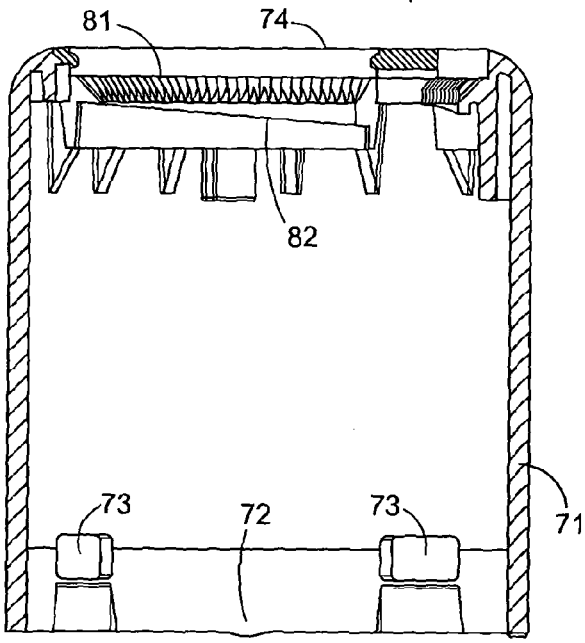

With reference to FIGS. 5 to 7, a dispenser cap 71 has a plurality of openings 73 shaped and configured to engage with the protrusions 51 on the main body part 6 so that the dispenser cap and main body part remain affixed to one another. The lower open end 72 (the dispenser cap is shown upside down in FIG. 5) is shaped and dimensioned to receive the portion of the can that extends from the main body part when mounted in the main body part. The dispenser cap may also be shaped and dimensioned to receive a counter mechanism between the dispenser cap and the can. Before assembly with the dispenser cap closure device, the dispenser cap has an open upper end 74.

A plurality of teeth 81 is provided along an upper part of the dispenser cap. These teeth are configured to engage with the dispenser cap closure device to prevent rotation once the latter is in the correct position. Preferably, the teeth are provided at least partially around the circumference of the upper part of the dispenser cap. This will be described in more detail below. In preferred embodiments, there are three toothed sections around the circumference of the upper part of the dispenser cap, with gaps 75 between each section. Each toothed section has a lower ramped surface 82. Again, this will be described in more detail with reference to the dispenser cap closure device.

One or more protrusions 91 may also be provided along an upper part of the dispenser cap 71, which are arranged to engage with a correspondingly shaped portion of the dispenser cap closure device 100 to help retain the dispenser cap closure device in place once inserted into the end of the dispenser cap. In preferred embodiments, there is one protrusion 91 for each gap 75.

We will now describe a cap closure device (or 'bung') that works with the above-described dispenser cap 71 to close the end of the dispenser, and take up any tolerances in the length of the container.

Figure 8:
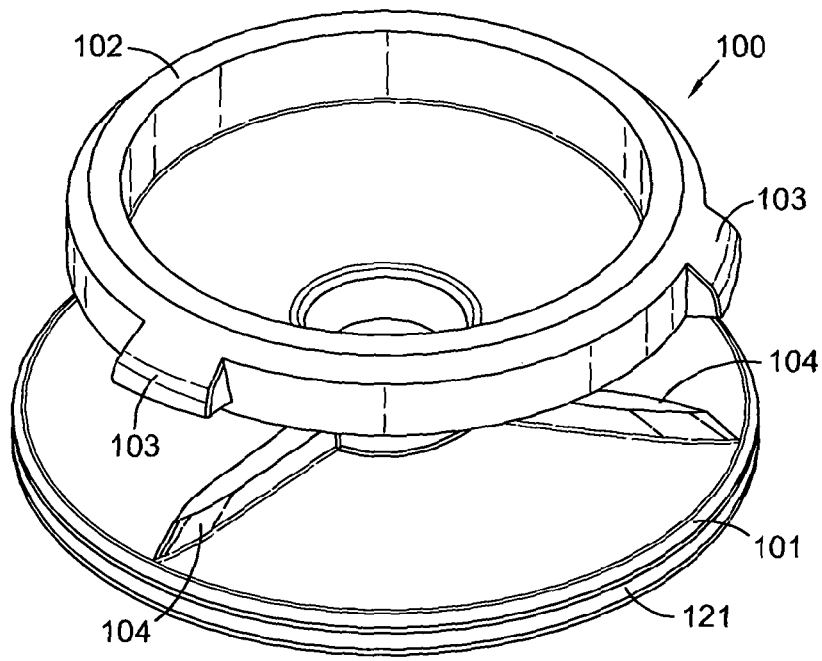
FIG. 8 is a preferred dispenser cap closure device.
Figure 9:
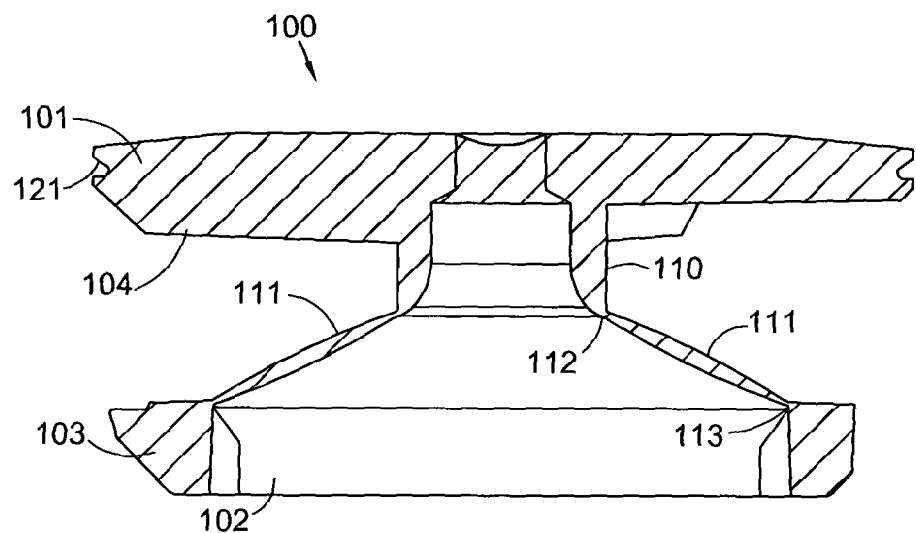
FIG. 9 is a cut-through view along the X-X line of the dispenser cap closure device of FIG. 8.

With reference to FIGS. 8 to 10, the dispenser cap closure device 100 comprises an upper cap closure portion 101 and a lower cap closure portion 102. The upper 101 and lower 102 cap closure portions are separated by a bistable portion 110, 111, 112, 113. The upper cap closure portion 101 comprises a plurality of radial extending ribs or ridges 104 located on an underside or lower surface of the upper cap closure portion 101. The upper cap closure portion 101 is configured to engage with the upper open end 74 of the dispenser cap 71 and to close the upper open end 74 when the two are engaged. Protrusions in the form of radial extending ribs or ridges 104 are configured to engage with the teeth 81 on the upper lip of the dispenser cap 71 to prevent rotation of the dispenser cap closure device 100 when engaged with the dispenser cap 71. Furthermore, ridge 121 in the circumferential edge of the upper cap closure portion 101 is configured to engage with the protrusions 91 in the dispenser cap 71 to help retain the dispenser cap closure device in place once inserted into the end of the dispenser cap.

The lower cap closure portion 102 has a lower surface that is configured to contact the end of a canister C in the dispenser when the dispenser cap closure device is engaged with the dispenser cap. A plurality of protrusions 103 are also located radially around the lower cap closure portion. The protrusions 103 are configured to engage with the ramped portion 82 of the dispenser cap 71 as will be described below.

The bistable portion 110, 111, 112, 113 comprises a substantially rigid separator 110 and a resiliently deformable separator 111. The substantially rigid separator 110 is fixed to or integral with the upper cap closure portion 101. The resiliently deformable separator 111 is connected to the substantially rigid separator 110 at one end by means of a resiliently deformable joint 112, and the resiliently deformable separator 111 is connected to the lower cap closure portion 102 at the other end by means of a resiliently deformable joint 113.

Figure 10A:
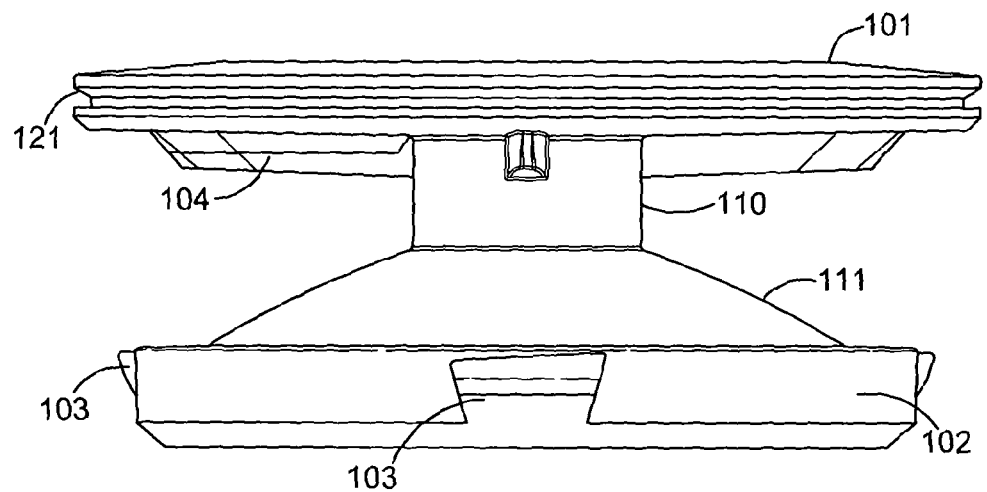
FIG. 10a is the dispenser cap closure device of FIG. 8 in an extended state.
Figure 10B:
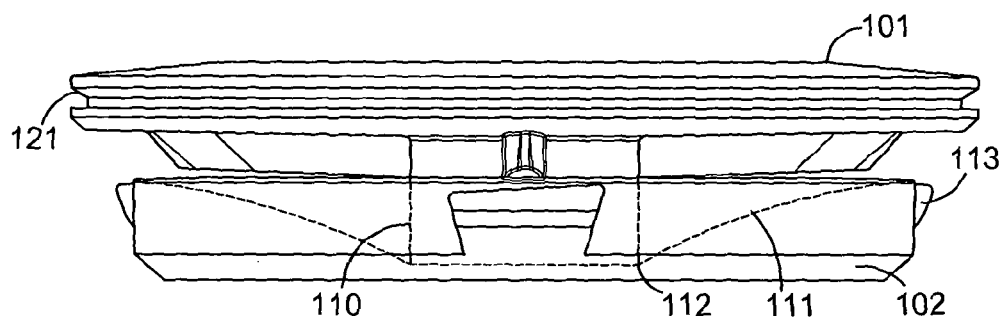
FIG. 10b is the dispenser cap closure device of FIG. 8 in a collapsed state.

The structure of the resiliently deformable separator 111 and resiliently deformable joints 112, 113 are configured to enable the dispenser cap closure device to switch or invert between a first stable form in which the bistable portion is extended (shown in FIG. 10a) and a second stable form in which the bistable portion is collapsed (shown in FIG. 10b). The upper 101 and lower 102 portions of the dispenser cap closure device are brought closer together in the second stable form (i.e. collapsed state). As can be seen in FIGS. 10a and 10b, an angle between the outer surface of the substantially rigid separator 110 and the outer surface of the resiliently deformable separator 111 is generally obtuse when the cap closure device is in the first stable form, and generally acute when the cap closure device is in the second stable form. The purpose of these two stable forms will be explained below.

The structure of the resiliently deformable separator 111 and resiliently deformable joints 112, 113 are configured such that the bistable portion, once in one of the two stable forms, remains in that stable form. A force applied to the upper 101 cap closure portion is required to switch the bistable portion from the first to the second stable form. Effectively, the force required to switch the bistable portion is proportional to the force required to deform the resiliently deformable separator 111 sufficiently such that the resiliently deformable separator 111 may pass through a substantially horizontal position (for example see FIGS. 9 and 10), which coincides with the shortest distance between the resiliently deformable joints 112, 113.

The dispenser cap assembly comprising the dispenser cap 71 and dispenser cap closure device 100 will now be described with reference to FIGS. 11a to 11f.

In FIG. 11a, the dispenser cap 71 is affixed to the main body part 6 of the dispenser (not shown). The upper open end of the dispenser cap is configured to receive the canister or container C, which is inserted through the upper opening and the spout S is seated in the junction member 41 in the body (not shown). Alternatively, the container C may be located before the dispenser cap 71 is affixed to the main body part 6.

In FIGS. 11b, 11c and 11d (once the canister C is seated correctly), the dispenser cap closure device 100 (in its first stable form i.e. extended) is lowered into the upper open end of the dispenser cap 71 until the lower cap closure portion 102 is seated on the end of the canister C. In order for this to happen, each of the protrusions 103 on the lower portion 102 is aligned with a corresponding gap 75 between the toothed sections or the upper open end of the cap, which allows the cap closure device 100 to drop through to the canister C.

In FIG. 11e, the cap closure device 100 is rotated. In doing so, protrusions 103 engage with the ramped surface 82 under each of the toothed sections 81. Each of the ramped portions 82 are configured such that rotation of the cap closure device 100 in one direction drives the protrusions (and therefore the cap closure device) downwards towards the canister C, which draws the cap closure device 100 further into the dispenser cap 71. Furthermore, this downward drive pushes the lower cap closure portion 102 against the end of the canister C. Continued rotation beyond an initial contact between the protrusion 103, ramped portion 82 and the end of the canister will apply a positive force in a longitudinal axis of the dispenser against the canister.

The amount of rotation of the dispenser cap closure device 100 is dependent upon the length of the canister and/or its spout (i.e. the tolerances that are being negated), and whether or not a positive pressure on the canister is desirable. During assembly, the amount of rotation can be determined in advance of the dispenser cap closure device 100 being inserted (for example by measuring the height of the end of the canister relative to the body), and the assembly machinery could be configured to turn the cap closure device a specific number of degrees of rotation (assuming that the slope of the ramped portion 81 is known). Alternatively, a force measuring device could be used during assembly to measure a back force registering on the cap closure device 100 when it is being rotated (or an increase in torque required to turn the cap closure device), with the machine being configured to stop rotation when a registered force reaches a threshold or desired level.

In FIG. 11f, and once the desired rotation of the cap closure device 100 has been reached, the upper portion 101 of the cap closure device is pushed down towards the canister such that is switches from the first stable form (i.e. extended) to the second stable form (i.e. collapsed). In the second stable form (as shown), radially extending ribs or ridges 104 on the underside of the upper portion 101 engage with the teeth portions 81 on the upper end of the dispenser cap 71. Such engagement between the ribs or ridges 104 and teeth portions 81 prevent further rotation (in either direction) of the cap closure device 100. Furthermore, protrusions 91 in the dispenser cap 71 engage with the ridge 121 in the upper cap closure portion 101 to help retain the dispenser cap closure device in place once inserted into the end of the dispenser cap. Since pressurised containers C generally have concave ends, the cap closure device 100 may extend below the original level of the lower portion 102 into the concave portion of such containers.

It will be noted that, since a force is required to deform the resiliently deformable separator 111 to overcome the horizontal position as described above (and therefore switch the bistable portion from the second to the first stable form), the dispenser cap closure device 100 is prevented from opening of its own accord. As such, once the dispenser cap closure device is in the second stable form, it is very difficult to undo or remove the device, which increases safety and security of the dispenser, since it makes it difficult for the user to tamper or take the dispenser apart.

In preferred embodiments, the dispenser cap 71 is transparent so that a counter can be read from beneath the surface. Alternatively, a transparent portion defining a window may be provided on the dispenser cap. Preferably, the dispenser cap 71 is made from polypropylene (for example R7051-10N).

In preferred embodiments, the dispenser cap closure device 100 is made from polypropylene (for example ELTEX 200CA25).

In an alternative embodiment of the closure device, the closure device works in the opposite way to the ways described above i.e. the closure device engages in the extended form rather than the contracted form.

FIG. 12 illustrates the alternative closure device. The lower cap closure portion 102' engages with the dispenser cap 71' as described above i.e. with the protrusions 103' riding on the lower surface of a ramped portion, and the lower cap closure portion 102' contacting a container (not shown) in the dispenser. The cap closure device is rotated or screwed into the correct position (to allow for the variation in height of the container) as above.

A substantially rigid separator 110' separates the lower closure portion 102' from the upper closure portion 101, which comprises a resiliently deformable section 120. The figure shows the closure device in the first, collapsed, form. Once the closure device is in place, a force may be applied to the resiliently deformable section 120, which causes the section to switch from the first, collapsed, stable form to a second, extended, stable form. In the extended form, the length of the upper closure portion is extended such that the upper closure portion engages with the dispenser cap 71' to close the upper open end of the dispenser cap.

As with the previous embodiments, protrusions may be located on a surface of the upper closure portion 101' to engage with correspondingly-shaped teeth located on the dispenser cap 71' to prevent further rotation of the cap closure device when engaged with the dispenser cap.

Whilst we have described the invention in the context of a dispenser cap closure arrangement, or the dispenser cap closure device, we also envisage uses for the closure arrangement and closure device on articles other than with medicament dispensers.

For example, the closure arrangement could be adapted to enclose or store an article, for example to close a container into which articles may be placed. In such uses, the container could be adapted to receive the closure device by providing the teeth 81 and ramped portions 82 at an upper open end of the container to engage with the corresponding features of the closure device (as described above with reference to the dispenser).

Since the closure device in such an alternative usage might not come into contact with a body such as a medicament container (to provide a suitable abutment surface to enable the bistable portion to be switched from the first stable form to the second stable form), an alternative could be to provide a surface (for example a protruding or raised surface on an inner circumferential surface of the container) to which the lower portion of the closure device could abut to enable the bistable portion to be switched. Furthermore, the surface could be configured to provide a seal to close the container when the closure device is in place and in the second (i.e. collapsed) stable form (i.e. when the lower closure portion of the closure device abuts the protruding surface).

In some embodiments, the seal between the protruding surface and the lower portion of the closure device could be arranged to provide a fluid and/or air-tight seal between the inside and outside of the container. In such embodiments, the container could therefore be used to contain liquids and/or gasses at atmospheric pressure, at a higher pressure (for example carbonated drinks, sparkling wines and the like) or at a reduced pressure (for example, vacuum sealing).

Articles stored in such a container at atmospheric, or reduced atmospheric air pressures, would not influence the cap closure device, since the bistable portion retains the closure device in the second (collapsed) stable form where the teeth in the container are engaged with the ridges or fingers 104 on the closure device.

If the internal pressure of the container is greater than atmospheric pressure, then the closure device may need to be modified in order to remain in the collapsed configured when the closure arrangement is closed. In the above-described embodiments, the closure device has an open lower end exposing a portion of the bistable portion to the contents of the container being enclosed. If the internal pressure of the sealed container is sufficient enough to overcome the force required to switch the bistable portion from the collapsed to the extended positions, the closure device would not work.

However, a modification to overcome this problem could be to provide a sufficiently rigid surface below the bistable portion on the lower closure portion to take the force of the pressure of the container, and prevent that pressure from influencing the bistable portion. Such a surface could be in line with the lower closure portion, or could extend below the lower closure portion.

The closure device may also be adapted to be openable by providing a handle attached to the upper closure portion in order to allow the user to pull the upper closure portion away from the container (thus switching the bistable portion back to the first, extended form) and thus unscrew the closure device from the lid of the container. In order to make this type of closure tamper resistant, or child proof, the handle could be removable, for example using a screw fixing, or a slide mechanism to attach the handle to the closure device.

We therefore envisage that the closure arrangement may be provided on items such as bottles for containing liquids, containers for containing articles and the like.

While the invention has been exemplified by the above description of specific embodiments, and uses thereof, the foregoing should not be considered by the reader as a limitation on the scope of the invention, which is defined in the appended claims.

The invention claimed is:

1. A dispenser cap arrangement for enclosing a portion of a dispenser of a medicament, the dispenser cap arrangement comprising:

a dispenser cap comprising a hollow body having a lower open end for engaging with a body portion of the dispenser, and an upper open end for receiving a cap closure device for closing the upper open end, the upper open end comprising an engageable portion; and the cap closure device, comprising:

an upper cap closure portion for engaging with the upper open end of the dispenser cap to close the upper open end of the dispenser cap;

a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap; and wherein the lower cap closure portion comprises a plurality of protrusions extending radially outwards having an upper surface for engaging with the engageable portion of the dispenser cap, and wherein a lower surface of the lower cap closure portion is engageable with a surface of a medicament container in the dispenser.

2. A dispenser cap arrangement according to claim 1, wherein the bistable portion of the cap closure device comprises:
   a substantially rigid separator connected to the upper cap closure portion; and
   a resiliently deformable separator having first and second ends, the first end being connected to the substantially rigid separator via a resiliently deformable joint, and the second end being connected to the lower cap closure portion via a resiliently deformable joint,
   wherein the resiliently deformable separator is configured to resiliently deform upon application of a force to the upper cap closure portion and lower cap closure portion so as to permit a change of form of the dispenser cap closure device between the first stable form and second stable form.

3. A dispenser cap arrangement according to claim 2, wherein an angle defined between an outer surface of the substantially rigid separator and the resiliently deformable separator is acute when in the second stable form, and obtuse when in the first stable form.

4. A dispenser cap arrangement according to claim 1, wherein the engageable portion of the dispenser cap comprises a ramped portion, and wherein the ramped portion and the protrusions on the lower cap closure portion are configured such that rotation of the cap closure device causes the upper surface of the plurality of protrusions to ride along the ramped portion so as to draw the cap closure device further into the dispenser cap.

5. A dispenser cap arrangement according to claim 4, wherein, when the cap closure device is rotated, the riding of the upper surface of the protrusions along the ramped portion causes the lower surface of the lower cap closure portion to drive down onto the medicament container in the dispenser.

6. A dispenser cap arrangement according to claim 4, wherein the ramped portion comprises a plurality of ramped portions around a circumference of a lip of the dispenser cap, the plurality of ramped portions equalling the number of plurality of protrusions on the lower cap portion of the cap closure device.

7. A dispenser cap arrangement according to claim 6, wherein the ramped portions are separated from one another by a gap having a width that is greater than or equal to a width of one of the plurality of protrusions on the lower cap closure portion.

8. A dispenser cap arrangement according to claim 1, wherein an upper surface of the dispenser cap comprises a limiting means for preventing rotation of the cap closure device when in the second stable form.

9. A dispenser cap arrangement according to claim 8, wherein the limiting means comprises a plurality of teeth located on the upper surface of the dispenser cap, and wherein the dispenser cap closure device comprises a plurality of protrusions on a lower surface of the upper cap closure portion, the teeth and protrusions being configured to engage with one another so as to prevent rotation of the cap closure device when in the second stable form.

10. A dispenser cap arrangement according to claim 1, wherein the dispenser cap comprises one or more protrusions in the upper open end of the dispenser cap, the one or more protrusions being arranged to engage with a correspondingly shaped recess in the upper cap closure portion when the dispenser cap is closed by the dispenser closure device.

11. A dispenser cap closure device for closing an end of a dispenser cap of a medicament dispenser, the cap closure device comprising:
   an upper cap closure portion for engaging with an upper open end of the dispenser cap to close an open end of the dispenser cap;
   a lower cap closure portion for engaging with an engageable portion of the upper open end of the dispenser cap to secure the cap closure device to the dispenser cap; and
   a bistable portion connecting the upper cap closure portion and the lower cap closure portion, the bistable portion being switchable between a first stable form in which the bistable portion is extended, and a second stable form in which the bistable portion is collapsed,
   wherein, when in the second stable form, the upper cap closure portion and lower cap closure portion are brought closer together; and
   wherein the lower cap closure portion comprises a plurality of protrusions extending radially outwards having an upper surface for engaging with the engageable portion of the dispenser cap, and wherein a lower surface of the lower cap closure portion is engageable with a surface of a medicament container in the dispenser.

12. A dispenser cap closure device according to claim 11, wherein the bistable portion comprises:
   a substantially rigid separator connected to the upper cap portion; and
   a resiliently deformable separator having first and second ends, the first end being connected to the substantially rigid separator via a resiliently deformable joint, and the second end being connected to the lower cap closure portion via a resiliently deformable joint,
   wherein the resiliently deformable separator is configured to resiliently deform upon application of an opposing force between the upper cap closure portion and lower cap closure portion so as to permit a change of form of the dispenser cap closure device between the first stable form and second stable form.

13. A dispenser cap closure device according to claim 12, wherein an angle defined between an outer surface of the substantially rigid separator and the resiliently deformable separator is acute when in the second stable form, and obtuse when in the first stable form.

14. A dispenser cap closure device according to claim 11, wherein the protrusions are substantially equally-spaced circumferentially around the lower cap closure portion.

15. A dispenser cap closure device according to claim 11, comprising a plurality of protrusions on a lower surface of the upper cap closure portion for engaging with correspondingly-spaced teeth on the dispenser cap for preventing rotation of the dispenser cap closure device when in the collapsed state.

16. A dispenser cap closure device according to claim 11, wherein the upper cap closure portion comprises a recess in the upper cap closure portion that is arranged to engage with a correspondingly shaped protrusion in the upper open end of the dispenser cap.

17. A dispenser for dispensing a dose of a medicament from a substance source, the dispenser comprising:
   a body for receiving the substance source, the body having a mouthpiece through which the medicament is dispensable;

the substance source comprising a container containing the medicament to be dispensed;

a dispenser cap arrangement according to claim 1, the dispenser cap arrangement being coupled to the body for enclosing the substance source.

18. A dispenser according to claim 17, wherein the substance source is a pressurised metered-dose inhaler (pMDI).

19. A dispenser according to claim 17, further comprising a dose counter for indicating a number of actuations of the dispenser corresponding to a number of doses dispensed from the substance or, or a number of doses remaining in the substance source.

20. A closure arrangement for enclosing an article, the closure arrangement comprising:

a hollow body for enclosing the article, having an upper open end for receiving a closure device for closing the upper open end, the upper open end comprising an engageable portion; and the closure device, comprising:

an upper closure portion for engaging with the upper open end of the hollow body to close the upper open end of the hollow body;

a lower closure portion for engaging with the engageable portion to secure the closure device to the hollow body; and a bistable portion connecting the upper closure portion and the lower closure portion, the bistable portion being switchable between a first stable form in which the bistable portion is extended, and a second stable form in which the bistable portion is collapsed, wherein, when the bistable portion is in the second stable form, the upper closure portion engages with the upper open end of the hollow body to close the upper open end of the hollow body such that the article in the hollow body is enclosed; and wherein the lower closure portion comprises a plurality of protrusions extending radially outwards having an upper surface for engaging with the engageable portion of the hollow body, and wherein a lower surface of the lower closure portion is engageable with a surface of the article to be enclosed.

21. A closure arrangement according to claim 20, wherein the bistable portion of the closure device comprises:

a substantially rigid separator connected to the upper closure portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of a force to the upper closure portion so as to permit a change of form of the closure device between the first stable form and second stable form.

22. A closure arrangement according to claim 21, wherein an angle defined between an outer surface of the substantially rigid separator and the resiliently deformable separator is acute when in the second stable form, and obtuse when in the first stable form.

23. A closure arrangement according to claim 20, wherein the engageable portion comprises a ramped portion, and wherein the ramped portion and protrusions on the lower closure portion are configured such that rotation of the closure device causes the upper surface of the plurality of protrusions to ride along the ramped portion so as to draw the closure device further into the hollow body.

24. A closure arrangement according to claim 23, wherein, when the closure device is rotated, the riding of the upper surface of the protrusions along the ramped portion causes the lower surface of the lower closure portion to drive down onto the article to be enclosed.

25. A closure arrangement according to claim 23, wherein the ramped portion comprises a plurality of ramped portions around a circumference of a lip of the hollow body, the plurality of ramped portions equalling the number of plurality of protrusions on the lower closure portion of the closure device.

26. A closure arrangement according to claim 25, wherein the ramped portions are separated from one another by a gap having a width that is greater than or equal to a width of one of the plurality of protrusions on the lower closure portion.

27. A closure arrangement according to claim 20, wherein the upper surface of the hollow body comprises a limiting means for preventing rotation of the closure device when in the second stable form.

28. A closure arrangement according to claim 27, wherein the limiting means comprises a plurality of teeth located on the upper surface of the hollow body, and wherein the closure device comprises a plurality of protrusions on a lower surface of the upper closure portion, the teeth and protrusions being configured to engage with one another so as to prevent rotation of the closure device when in the second stable form.

29. A closure arrangement according to claim 20, wherein the hollow body comprises one or more protrusions in an upper open end of the hollow body, the one or more protrusions being arranged to engage with a correspondingly shaped recess in the upper closure portion when the hollow body is closed by the closure device.

* * * * *